US011850028B2

(12) United States Patent
Sheldon et al.

(10) Patent No.: US 11,850,028 B2
(45) Date of Patent: Dec. 26, 2023

(54) MULTI-SENSOR BIOMETRIC INFORMATION MONITORING DEVICE

(71) Applicant: 42 Health Sensor Holdings LTD, Calgary (CA)

(72) Inventors: Robert Stanley Sheldon, Calgary (CA); Daniel Edward Roach, Calgary (CA)

(73) Assignee: 42 Health Sensor Holdings LTD, Calgary (CA)

( * ) Notice: Subject to any disclaimer, the term of this patent is extended or adjusted under 35 U.S.C. 154(b) by 295 days.

(21) Appl. No.: 17/205,196

(22) Filed: Mar. 18, 2021

(65) Prior Publication Data

US 2021/0290079 A1 Sep. 23, 2021

Related U.S. Application Data

(60) Provisional application No. 62/991,239, filed on Mar. 18, 2020.

(51) Int. Cl.
*A61B 5/0205* (2006.01)
*A61B 5/00* (2006.01)
(Continued)

(52) U.S. Cl.
CPC ...... *A61B 5/02055* (2013.01); *A61B 5/02007* (2013.01); *A61B 5/05* (2013.01);
(Continued)

(58) Field of Classification Search
CPC ... A61B 5/02055; A61B 5/02007; A61B 5/05; A61B 5/318; A61B 5/6803;
(Continued)

(56) References Cited

U.S. PATENT DOCUMENTS

| 2010/0217099 A1* | 8/2010 | LeBoeuf | A61B 5/021 600/301 |
| 2013/0079647 A1* | 3/2013 | McGonigle | A61B 5/7239 600/300 |

(Continued)

FOREIGN PATENT DOCUMENTS

| CN | 108926336 | * 12/2018 | ......... A61B 5/02141 |
| JP | 2006102188 | * 4/2006 | |
| JP | 2006-212178 | 8/2006 | |

OTHER PUBLICATIONS

Anusha, "Wireless Communication: Introduction, Types and Applications", Electronics Hub, published Jun. 8, 2017 at http://www.electronicshub.org/wireless-communication-introduction-types-applications (Year: 2017).*

(Continued)

*Primary Examiner* — Eric F Winakur
*Assistant Examiner* — Jonathan Drew Moroneso
(74) *Attorney, Agent, or Firm* — Meunier Carlin & Curfman LLC (57) ABSTRACT

An apparatus for monitoring biometric information blood of a user that contains a housing that includes an electropermanent magnet, a battery, a processor, and a radio transmitter. A cap is magnetically coupled to the housing when a current is passed through a coil of the electropermanent magnet thereby compressing a portion of tissue of the user between the housing and the cap. By varying the compressive force applied to the tissue, the apparatus monitors at least one of blood pressure and heart rate from the response.

10 Claims, 9 Drawing Sheets

(51) Int. Cl.
    *A61B 5/02*         (2006.01)
    *A61B 5/05*         (2021.01)

(52) U.S. Cl.
    CPC .......... *A61B 5/6803* (2013.01); *A61B 5/6815* (2013.01); *A61B 5/6838* (2013.01); *A61B 2560/0223* (2013.01); *A61B 2562/0219* (2013.01); *A61B 2562/0271* (2013.01); *A61B 2562/06* (2013.01)

(58) Field of Classification Search
    CPC ................ A61B 5/6815; A61B 5/6838; A61B 2560/0223; A61B 2562/0219; A61B 2562/0271; A61B 2562/06; A61B 5/021; A61B 5/02438
    See application file for complete search history.

(56) References Cited

U.S. PATENT DOCUMENTS

| | | |
|---|---|---|
| 2020/0155017 A1 | 5/2020 | Sheldon et al. |
| 2020/0330038 A1 | 10/2020 | Sheldon et al. |
| 2021/0228101 A1* | 7/2021 | Lehtonen ........... A61B 5/02433 |
| 2022/0395183 A1* | 12/2022 | Bogatu ............... A61B 5/7278 |

OTHER PUBLICATIONS

Hunter, "Electropermanent Magnets (EPMs)", mbedded.ninja, published Jun. 22, 2014 at https://blog.mbedded.ninja/electronics/components/electropermanent-magnets-epms/ (Year: 2014).*

Mitchell, "Arterial Stiffness and Hypertension, Chicken or Egg?", Hypertension, 64, 210-214, published Aug. 2014 (Year: 2014).*

International Search Report and Written Opinion, dated May 31, 2021, received in connection with corresponding International Patent Application No. PCT/IB2021/052285.

* cited by examiner

MULTI-SENSOR BIOMETRIC INFORMATION MONITORING DEVICE

CROSS-REFERENCE TO RELATED APPLICATION

This application claims priority to U.S. Provisional Patent Application No. 62/991,239, filed Mar. 18, 2020, entitled "Multi-Sensor Blood Pressure Monitoring Device," which is incorporated herein by reference in its entirety.

BACKGROUND OF THE DISCLOSURE

Field of Disclosure

The present disclosure relates generally to physiological monitoring devices, and in particular to a wearable multi-sensor blood pressure monitoring device.

Description of Related Art

In order to diagnose or monitor a patient experiencing syncope or hypertension, a physician requires patient blood pressure (BP) data. A measurement taken by the physician during an in-clinic appointment captures only the patient's blood pressure at the time of the reading and does not detect transient changes in blood pressure throughout a typical day. Often the one-time reading is insufficient, and thus BP data collected over an extended period is ordered by the physician. Typically, these data are collected using an ambulatory blood pressure (BP) monitor over a period of 24 hours.

A standard ambulatory BP monitor consists of an automatically inflatable cuff worn on the user's arm for the diagnostic period, connected by an air supply tube to a monitoring device. These monitors are cumbersome to wear and interfere with normal activity as they automatically inflate and squeeze the user's arm to measure blood pressure approximately every 15 to 30 minutes of the day. It is recommended that the user limit movement and sit down, if possible, when the cuff is inflating and taking a reading. Disadvantageously, a user may not experience a typical day when interrupted regularly with an inflating cuff. Additionally, with measurements taken at a specified time interval, the data collected is a series of individual measurements, rather than a continuous, uninterrupted stream of data, thereby not truly providing full blood pressure data over the monitoring period for the patient.

SUMMARY OF THE DISCLOSURE

The present disclosure is directed to an inexpensive, wearable, comfortable, robust device that directly and accurately measures blood pressure, heart rate, oxygen saturation, temperature, body motion, and time either continuously or semi-continuously, and transmits this to a base station that interacts with the Internet or other communications infrastructure.

In accordance with an aspect of the disclosure, an apparatus for monitoring biometric information of a user includes a clip having a base with two side members adapted to releasably receive a portion of tissue of the user therebetween, a multi-sensor mounted to one of said two side members, a motor operably connected to a plunger, and a processor that executes computer executable instructions stored in a memory. The motor is operably controlled by the processor to vary strain applied to the portion of the tissue over time to measure a response. The multi-sensor monitors at least one of blood pressure, heart rate, oxygen saturation, temperature, body motion from the response.

In accordance with another aspect of the disclosure, an apparatus for monitoring biometric information of a user includes a housing that includes an electropermanent magnet, a battery, a processor, and a radio transmitter. A cap on one side of the tissue is magnetically coupled to the housing on the other side of the tissue; when an electric DC current of programmed amperage and duration is passed through a coil of the electropermanent magnet, this transverse magnetic coupling strength is programmatically varied thereby allowing variable compression a portion of tissue of the user between the housing and the cap. A compressive force applied to the tissue is operably controlled by the processor which varies a magnetic field strength applied to the cap to measure a response of the tissue. The apparatus monitors at least one of blood pressure and heart rate from the response.

Other aspects and features of the present disclosure will become apparent to those ordinarily skilled in the art upon review of the following description of specific aspects of the disclosure in conjunction with the accompanying figures.

BRIEF DESCRIPTION OF THE DRAWINGS

In drawings which illustrate aspects of the disclosure wherein similar characters of reference denote corresponding parts in each view.

DETAILED DESCRIPTION

Introduction

Access to medical information should be easily acquired in the community, contextualized, personalized, and owned by the patient. The present disclosure achieves this by disclosing a small, portable, transcutaneous, continuously active, device that monitors biometric information such as, but not limited to, blood pressure, oxygen saturation, temperature, and/or body motion. The device is unique due to its size (about 1.5×1.5×2.5 cm and 10 gm) and ability to sample continuously for at least 24 hours to provide beat-to-beat BP, heart rate sensing and uninterrupted use. The device provides a convenient alternative to both Ambulatory Blood Pressure Monitoring (ABPM) and home BP monitoring, and as a research tool. The device is battery-powered, and through a wireless connection, data is transmitted and displayed on, e.g., a smartphone or personal computer.

Figure 1:
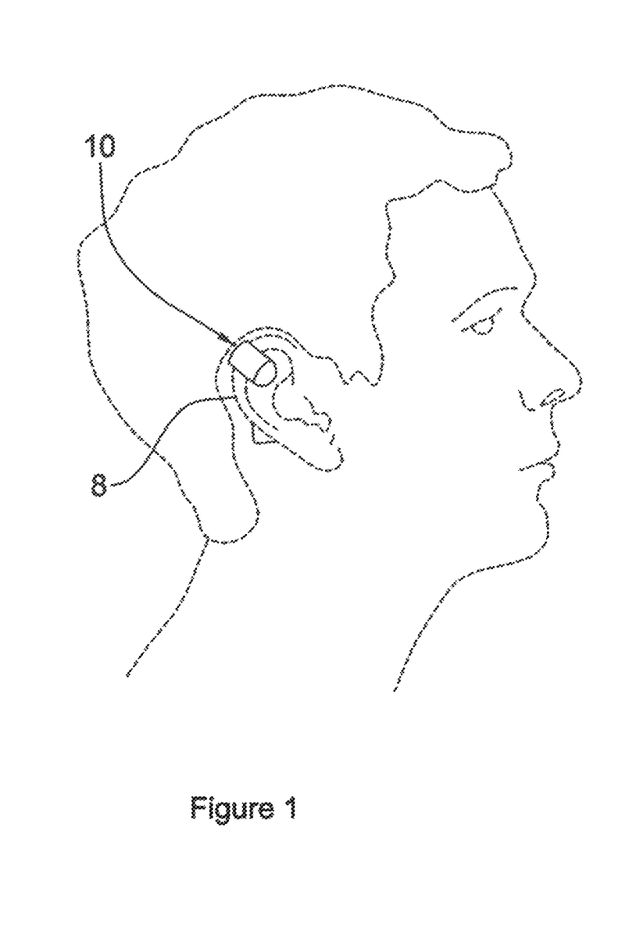
FIG. 1 is a side view of an apparatus for monitoring biometric information of a user clipped to a portion of the user's ear.
Figure 2:
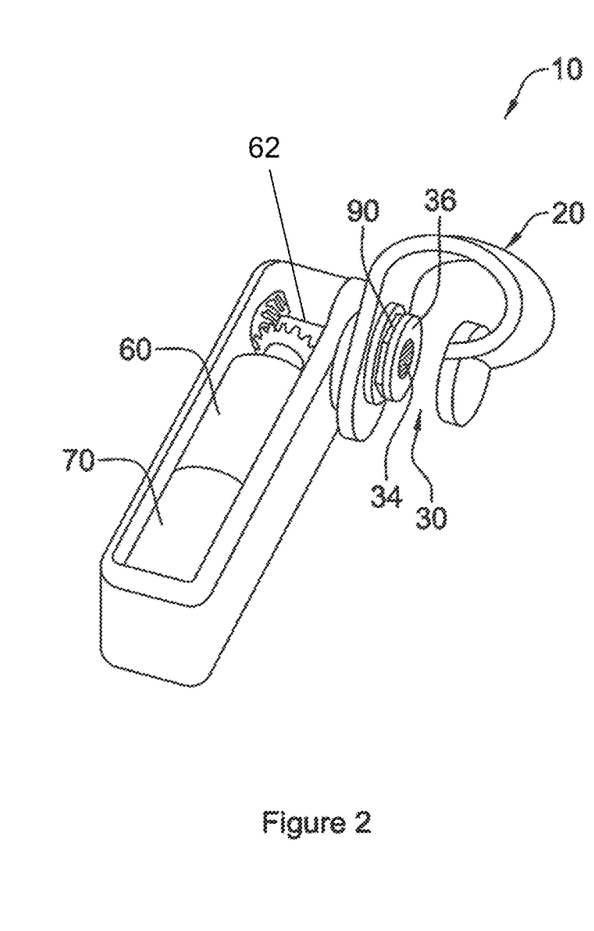
FIG. 2 is a perspective view of the apparatus of FIG. 1.

Referring now to FIGS. 1 and 2, there is shown an example device 10 for monitoring biometric information, such as, heart rate, oxygen saturation, temperature, body motion, etc., of a user. The device 10 is preferably clipped to a portion of a user's ear 8. The advantages of the ear pinna—the bulk of the visible external ear—include its proximity to the carotid artery and heart, its physical stability compared to for example the wrist, and the ability to compress it from both sides. The apparatus 10 includes a clip 20 rotatably connected to a drive housing 50. The clip 20 is adapted to receive a portion of a user's ear 8 within a gap 30. A multi-sensor 34 mounted to measure, e.g., an arterial pulsatile waveform and other biometric information. A motor 60 within the drive housing 50 is operably connected to a plunger 62, as described below. Although the apparatus 10 is illustrated clipped to an ear 8, it will be appreciated that it may be adapted to clip to other parts of a user's body having similar compressibility from both sides, such as, by way of non-limiting example, a finger.

Signal preprocessing and external transmission to/from the device 10 to a base station is achieved by using a low power radio transmitter, e.g., Bluetooth, NFC, or other radio communication technology. The base station may be any Android, Apple, or Microsoft PC device capable of receiving the information from the device 10. The radio transmitter preferably includes a highly accurate clock that can be synchronized externally. In addition, the information sent from the device 10 to the base station is exportable to other utilities, the cloud or other. A software development kit enables third parties to develop software to access the measurements.

Although not shown in the figures, the device 10 includes a battery that is small, rechargeable with a capacity of at least 63 mAh in order to meet the power demands of the numerous sensors, the computational signal preprocessing and communications transmission. The device 10 may transmit either continuously or discontinuously to a base station, and in an alternative, include flash RAM capable of recording at least 24 hours of biometric information.

To provide for long-term comfort, the gap 30 created by the clip 20 may be released every 10-20 minutes so that the ear tissue can rid itself of accumulated metabolites, etc. As the device 10 has precision control over the motor 60, the ear tissue may be "pumped" by rapidly tightening and loosening clip 20 across the ear tissue using the motor control. This will enhance long-term comfort and also help keep the tissue from getting overwhelmed by metabolites, thus preserving the "freshness" of the tissue (i.e., as close to natural state of the tissue as possible). This is preferable because the vascular tissue within the clip 20, in particular the vascular wall elasticity, plays a role in the generation of the blood pressure waveform.

In addition to the above, because the device provides 10 for precise control of the motor 60 in real-time, pre-programmed straining protocols may be applied (i.e., varying strain as a function of time). By controlling the strain protocols, strain oscillations at any number of frequencies, or even random strain, can be systematically applied across the vascular ear bed; this enables the device 10 to be an "active" sensor. By "active," it is meant that the device 10 is actively stimulating the tissue mechanically and measuring the tissue response using the force sensor. Thus, the device 10 can interrogate elastic properties of the arteries. For instance, applying varying frequencies of strain oscillations would show how the tissue responds at each frequency. Thus, a spectrum of the "elasticity" of the arterial beds within the ear vise may be produced. The measured "elasticity" may be tested as a function of disease state or pharmacological intervention to provide a completely new type of micro-measurement of vascular behavior. In addition, the motor control compensates for the visco-elastic effects of the polymer clip (i.e., stress-relaxation and polymer memory).

Figure 3:
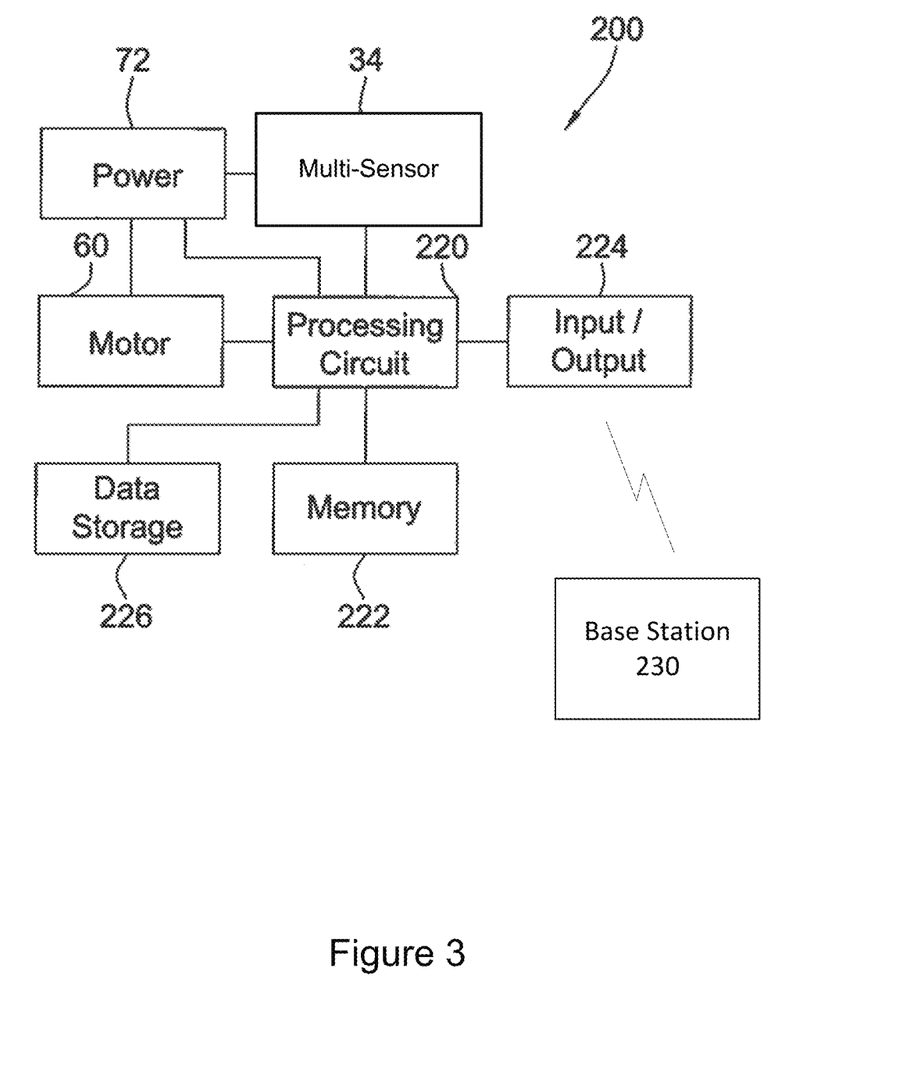
FIG. 3 is a block diagram of the control system for monitoring blood pressure of a user with the apparatus of FIG. 1.
Figure 4A:
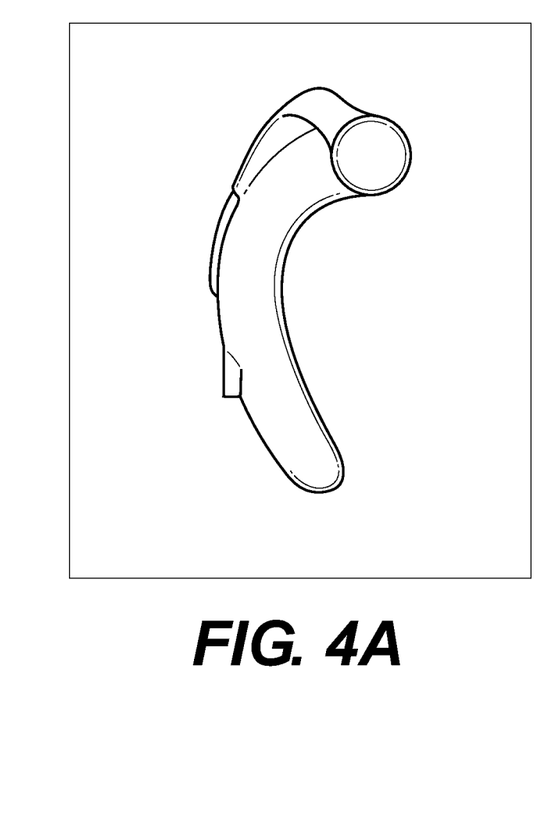
FIGS. 4A, 4B, 4C and 4D illustrate views of an example implementation of the apparatus of FIG. 1.
Figure 4B:
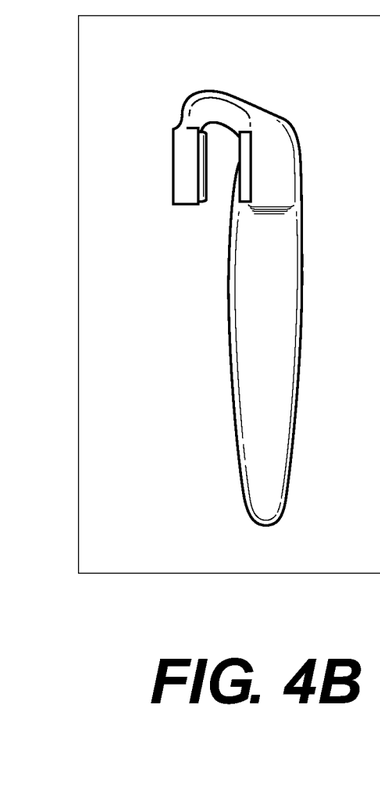
Figure 4C:
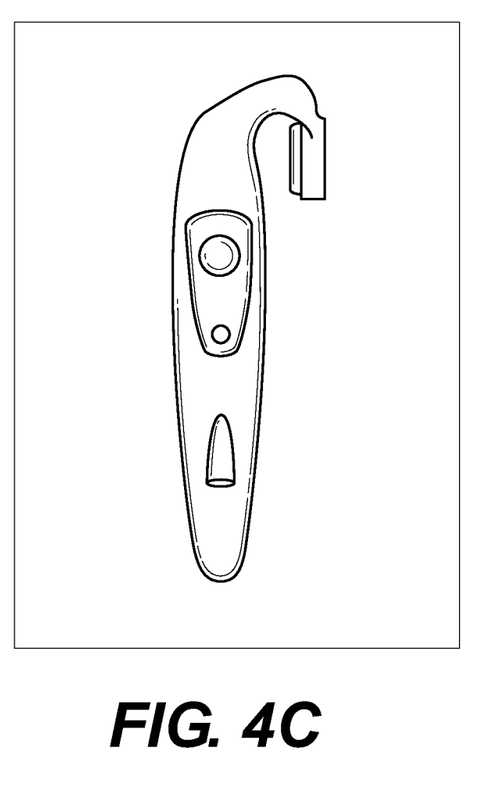
Figure 4D:
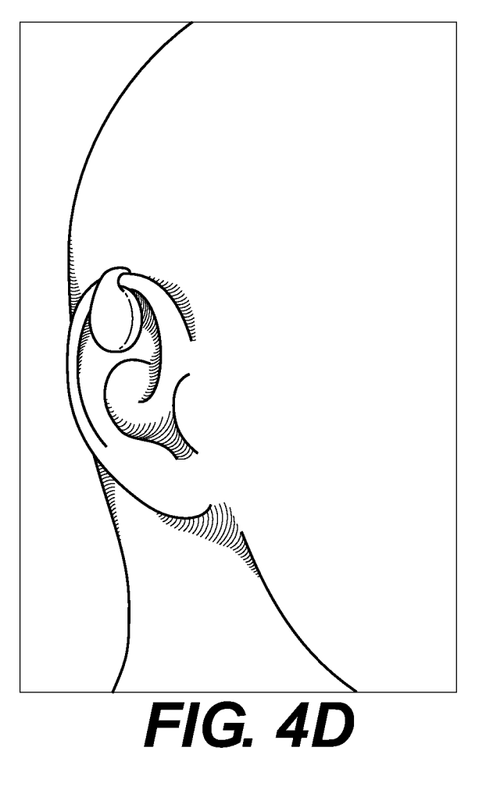

Turning now to FIG. 3, the apparatus 10 includes a control system 200. The processor 70, comprises a processing circuit 220 and memory 222 that stores machine instructions that, when executed by the processing circuit 220, cause the processing circuit 220 to perform one or more of the operations and methods described herein. The processing circuit 220 may optionally contain a cache memory unit for temporary storage of instructions, data, or computer addresses. The control system 200 further includes a data storage 226 of any conventional type operable to store a plurality of entries containing the waveform measurements received from the multi-sensor 34. It will be appreciated that the processing circuit 220 may contain instructions to convert the waveform measurements to blood pressure data or other, or the raw data received from the multi-sensor 34 may be stored within the data storage 226 and processed further into blood pressure data with a remote processor. Power is supplied to the multi-sensor 34 and processing circuit 220 with the motor 60 controlled by the processing circuit 220 to periodically extend and retract an adjustable pressure pad. The control system 200 also includes an input/output interface 224 such as the radio transmitter, ethernet adapter, USB connection or the like for providing communication between the processing circuit 220 and external systems, such as a base station 230, as described above.

More generally, in this specification, including the claims, the term "processing circuit" is intended to broadly encompass any type of device or combination of devices capable of performing the functions described herein, including (without limitation) other types of micro-processing circuits, microcontrollers, other integrated circuits, other types of circuits or combinations of circuits, logic gates or gate arrays, or programmable devices of any sort, for example, either alone or in combination with other such devices located at the same location or remotely from each other. Additional types of processing circuit(s) will be apparent to those ordinarily skilled in the art upon review of this specification, and substitution of any such other types of processing circuit(s) is considered not to depart from the scope of the present disclosure as defined by the claims appended hereto. In various aspects, the processing circuit 220 can be implemented as a single-chip, multiple chips and/or other electrical components including one or more integrated circuits and printed circuit boards.

Computer code comprising instructions for the processing circuit(s) 220 to carry out the various aspects, aspects, features, etc. of the present disclosure may reside in the memory 222. In various aspects, the processing circuit 220 can be implemented as a single-chip, multiple chips and/or other electrical components including one or more integrated circuits and printed circuit boards. The processing circuit 220 together with a suitable operating system may operate to execute instructions in the form of computer code and produce and use data. By way of example and not by way of limitation, the operating system may be Windows-based, Mac-based, or Unix or Linux-based, among other suitable operating systems. Operating systems are generally well known and will not be described in further detail here.

Memory 222 may include various tangible, non-transitory computer-readable media including Read-Only Memory (ROM) and/or Random-Access Memory (RAM). As is well known in the art, ROM acts to transfer data and instructions uni-directionally to the processing circuit 220, and RAM is used typically to transfer data and instructions in a bi-directional manner. In the various aspects disclosed herein, RAM includes computer program instructions that when executed by the processing circuit 220 cause the processing circuit 220 to execute the program instructions described in greater detail below. More generally, the term "memory" as used herein encompasses one or more storage mediums and generally provides a place to store computer code (e.g., software and/or firmware) and data that are used by the control system 200. It may comprise, for example, electronic, optical, magnetic, or any other storage or transmission device capable of providing the processing circuit 220 with program instructions. Memory 222 may further include a floppy disk, CD-ROM, DVD, magnetic disk, memory chip, ASIC, FPGA, EEPROM, EPROM, flash memory, optical media, or any other suitable memory from which processing circuit 220 can read instructions in computer programming languages.

FIGS. 4A-4D illustrate an example working implementation of the device 10. The example incorporates engineering details such as pressure plunger alignment, device physical stabilization, ear clip function, and an adhesive backing.

Figure 5:
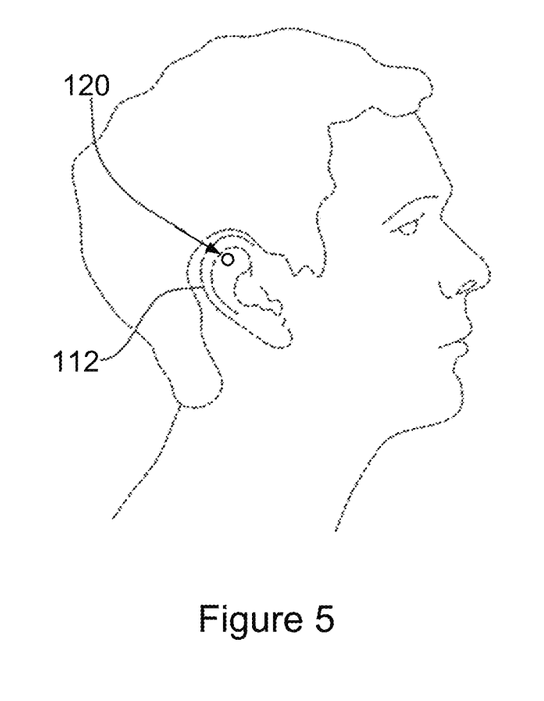
FIG. 5 is a side view of another apparatus for monitoring biometric information of a user clipped to a portion of the user's ear.
Figure 6:
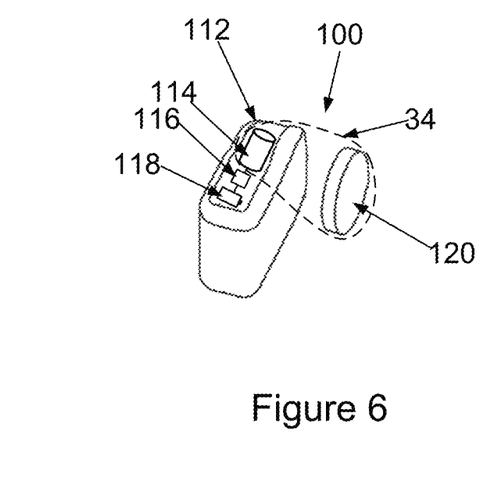
FIG. 6 is a perspective view of the apparatus of FIG. 5.

FIGS. 5 and 6 illustrate another example implementation of an apparatus to measure biometric information, such as, heart rate, oxygen saturation, temperature, body motion, etc., of a user. The device 100 includes housing 112 that houses an electropermanent magnet (EPM) 114, a processor 116, rechargeable battery 118 and a radio transmitter (not shown). The housing 112 is disposed behind the user's ear and is magnetically coupled to a cap 120 (e.g., a Rare Earth Element (REE) magnet or steel/iron cap) that is located on the outer surface of the user's ear. The cap 120 is integral to the device 100 and will self-centre due to symmetries in the EPM magnetic-field configuration across the ear tissue. Thus, the device 100 provides a monitoring solution with no moving parts. In operation, the compression force across the tissue applied by the electropermanent magnet 114 is controlled by setting the pulse-width (and thus maximum current) through a coil within the EPM 114, thereby configuring the EPM magnetic field across the ear tissue to the desired compression forces. The EPM uses a programmable static magnetic field to create force (and thus compression) across the ear tissue. This magnetic field couples the magnetic components of the housing and the cap, and the strength of this magnetic field will naturally vary is response to the forces created by pulsatile and non-pulsatile arterial blood pressure. A Hall Effect Transducer (HET) measuring some aspect of this pulsatile magnetic field would thus provide a calibratable proxy for the changing forces (and compression) across the ear tissue. This would obviate the need for a stress-transducer in the design, because the strength of the coupling magnetic field would correspond to a known force (and compression). The magnetically self-centering cap would ensure that the housing/cap geometry remains consistent across any tissue thickness, thus ensuring the fidelity of the magnetic field surrogate for force.

Similar to the device 10, signal preprocessing and external transmission to/from the device 100 to a base station is achieved by using a low power radio transmitter, e.g., Bluetooth, NFC, or other radio communication technology. The base station may be any Android, Apple, or Microsoft PC device capable of receiving the information from the device 100. The device 100 may transmit either continuously or discontinuously to a base station, and in an alternative, include flash RAM capable of recording at least 24 hours of biometric information.

To provide for long-term comfort, the magnetic field strength generated by the EPM 114 may be reduced every 10-20 minutes so that the ear tissue can rid itself of accumulated metabolites, etc. The device 100 may have other programmed force/pressure protocols which may relax or strengthen the magnetic field strength.

Figure 7:
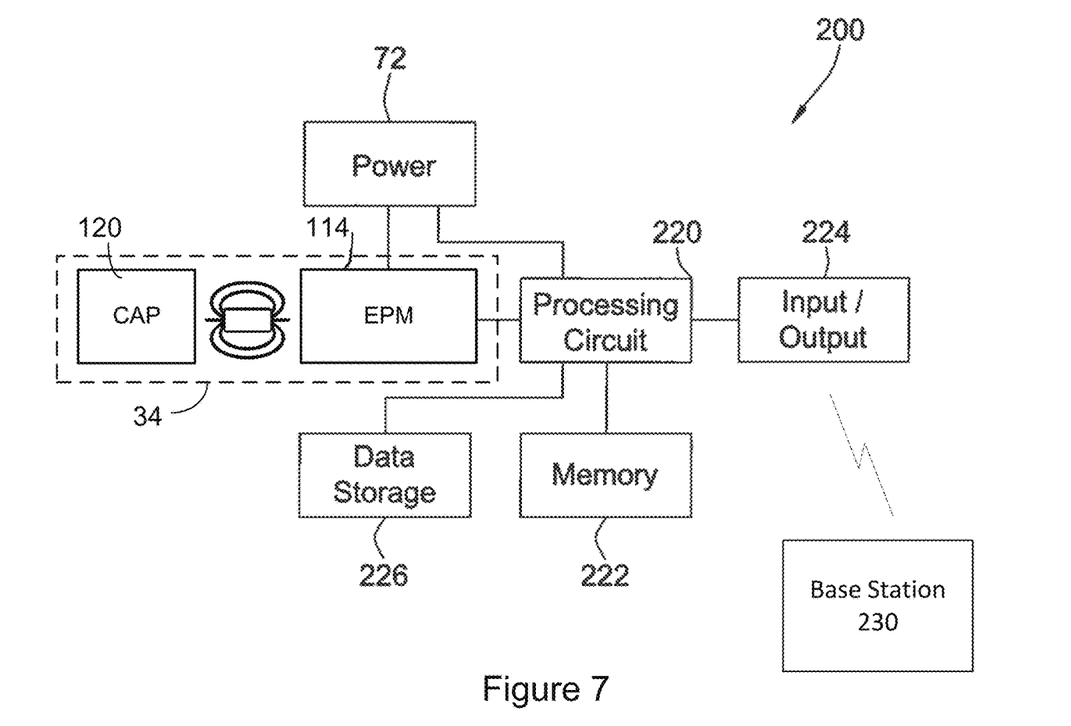
FIG. 7 is a block diagram of the control system for monitoring blood pressure of a user with the apparatus of FIG. 5.
Figure 8:
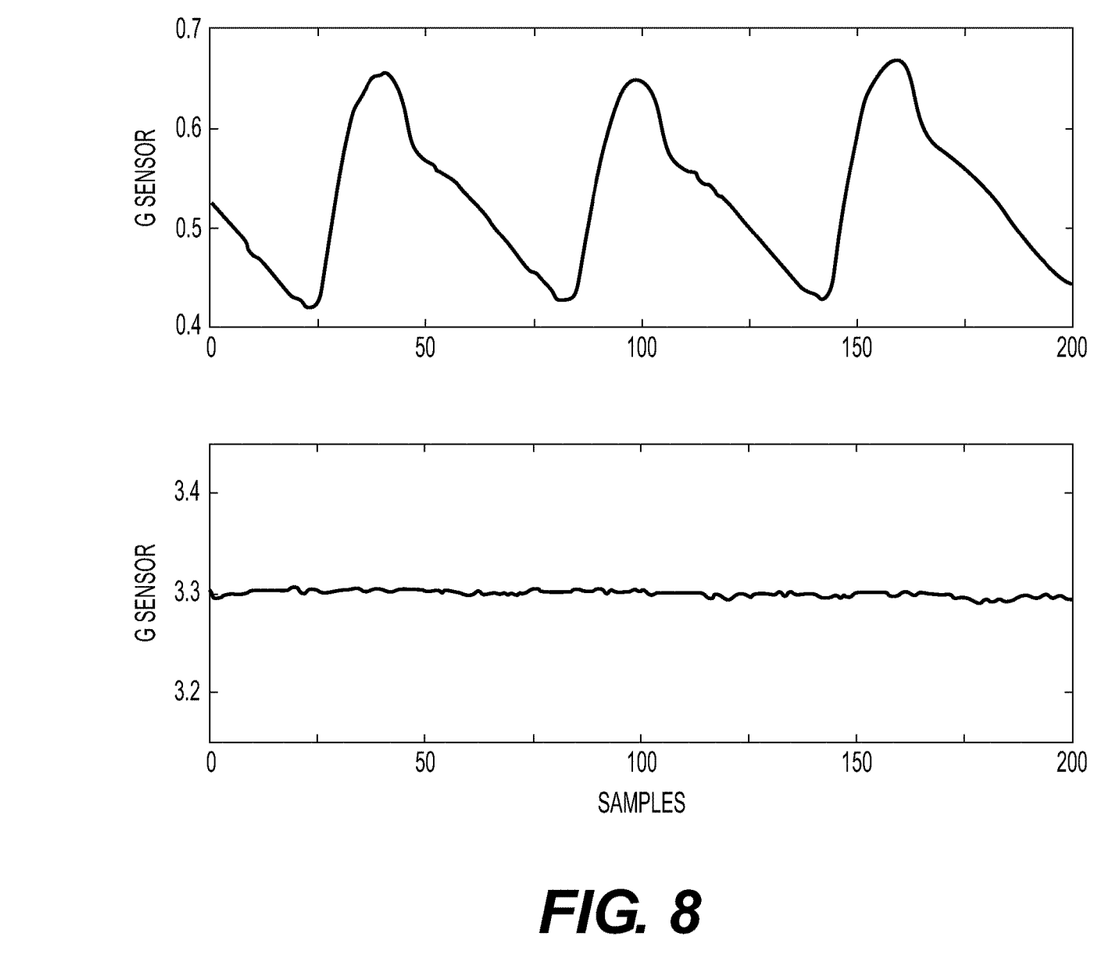
FIG. 8 shows pulse contours with and without an occluding pressure.
Figure 9:
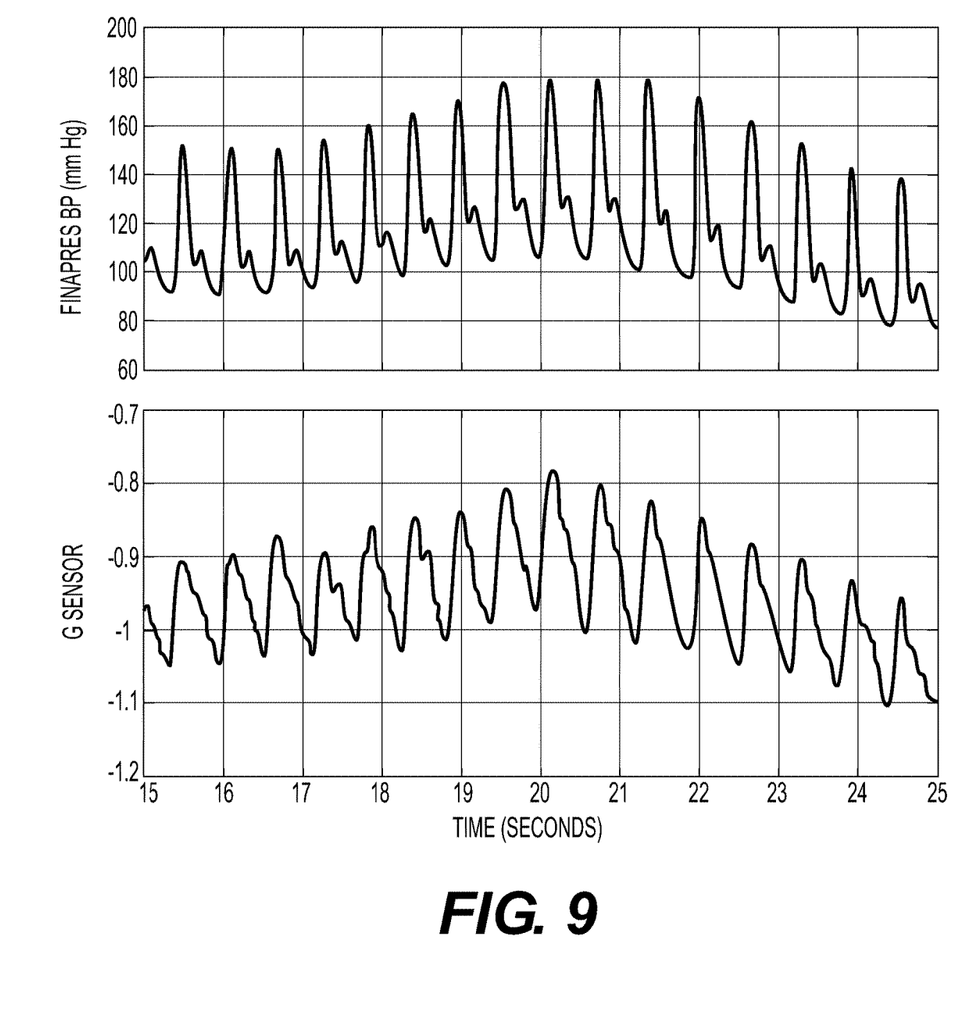
FIG. 9 shows a comparison of simultaneous sequences from the Finapres sensor (top) and the magnet sensor (bottom)
Figure 10:
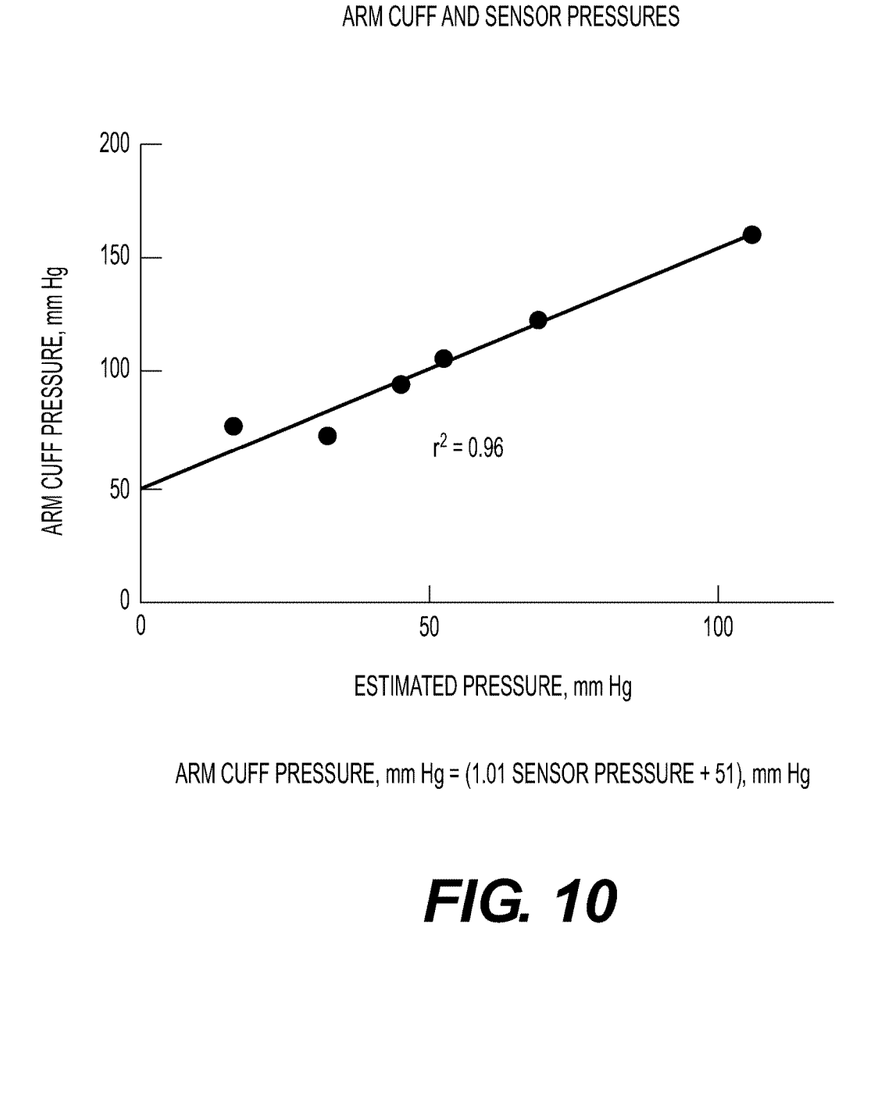
FIG. 10 shows a comparison of arm cuff and sensor pressures in 3 healthy subjects.

Turning now to FIG. 7, the apparatus 100 includes a control system 200, similar to device 10. In FIG. 7, like components already described above will not be repeated. The processor 116, comprises a processing circuit 220 and memory 222 that stores machine instructions that, when executed by the processing circuit 220, cause the processing circuit 220 to perform one or more of the operations and methods described herein. The processing circuit of the device 100 may be programmed to provide force/pressure protocols by varying the magnetic field coupling the cap 120 to the EPM 114. The protocols are achieved by varying the current supplied to the EPM coils.

Multi-Sensor 34

The multi-sensor 34 may acquire data related to one or more of blood pressure, oxygen saturation, temperature, and/or body motion. The multi-sensor may comprise plural sensors in either device 10 or device 100. Blood pressure sensing acquires pressure waveforms continuously and validates them discontinuously, and will be based on an information obtained by a MEMS force sensor or a magnetic sensor. Heart rate is detected accurately from analysis of the waveforms. Oxygen saturation, temperature, highly accurate time, body position and motion, are acquired using commercial off-the-shelf (COTS) or modified equipment. in some implementations of the device 10, sensors may be mounted in the plunger 62, such that the sensor face and the rest of the plunger vise face are coplanar.

With respect to all implementations described herein, it should be understood that sensors may be mounted anywhere in device 10 or device 100 to achieve a sensing functionality. For example, Hall Effect Transducers (HETs), which measure magnetic field strength, may saturate in the near vicinity of the REE magnets and near steel/iron components of the electro-permanent magnet 114. To avoid saturation of these super sensitive devices, the HETs may be mounted away from the high magnetic field which typically spans the tissue. Moreover, the HETS may be mounted off the co-axial axis, where the magnet field strength is weaker and not saturating the HETs. Because the magnetic field strength can be initially empirically determined at different locations in the device 10 or device 100, these non-saturated locations may be used as a proxy for the true magnet field strength (and force) across the tissue.

Blood Pressure Monitoring

The accurate and ongoing measurement of blood pressure is derived from a continuous waveform that resembles the carotid artery waveform. The signal is preferably stable, reasonably noise-free, not contaminated by extraneous signals, and whose derived systolic and diastolic blood pressure estimates can be validated rather than modeled. In one implementation using device 10, the multi-sensor 34 may utilize the motor 60 and plunger 62 for this purpose. For example, A COTS miniature gearbox motor and worm-gear drives an orthogonally mounted plunger that occludes ear arterial flow with known force and pressures. This permits calculation of systolic and diastolic pressures. It is equivalent to an arm blood pressure cuff.

In another implementation using device 100, the multi-sensor 34 may comprise the combination of the electropermanent magnet (EPM) 114 and cap 120 for both BP sensing and validation. As noted above, this is a form of permanent magnet in which is embedded an electromagnet in the form of a coil around a permanent magnet of lower intrinsic coercivity; the permanent magnet's magnetic field is reversed by a brief pulse of electric current. This magnetic field reversal causes rerouting of the magnetic flux within the electropermanent magnet structure. The EPM configuration can use this rerouted magnetic flux to latch between a high magnet field state, and a low magnetic field state, (based upon the electropermanent magnet geometry).

Varying current pulse widths from 10-100 microseconds can vary the desired force of the latched state and therefore permits computer-controlled electronic modulation of magnetic force. The necessary variables include the size and magnetic properties of the various permanent magnets, the area of the magnet face, the interface distance, and number of wire coils around the electropermanent magnet, the instantaneous current through the coil, and the current pulse width. Commercially available REE magnets will generate the Teslas and force necessary, and the battery has the power required to generate the brief current pulses required to latch the modulated states. The force generated and measured during arterial pulsations will be measured using a COTS miniature force sensor (e.g., the EPM), and the analogue force will be digitized using a COTS analogue-to-digital converter. The signal is communicated by the radio transmitter to the base station for, e.g., clinical analysis.

With an EPM, a Hall Effect Transducer (HET) may be used to detect the strength of the magnetic field across the tissue and between the coaxial magnetic components, be they REE magnets, EPM, or steel (or iron). The coaxial magnetic components are self-centering; the magnetic component (magnet or steel/iron) on the front side of the ear aligns itself with the near-field magnetic field properties of the magnetic components (magnet or steel/iron) behind the ear, together they produce a self-centered coaxial magnetic field. A HET can measure any portion of this coaxial field, and because the geometry is known, the strength of the magnetic field across the tissue can be accurately estimated and empirically validated, such that this field strength HET estimate can be used to estimate force across the tissue. Other potential EPM geometries may not be coaxial across the tissue but the HET placed anywhere near the magnetic field can be used in a similar way to estimate the magnetic field strength and force across the tissue.

Validating the blood pressure signal involves a good signal that is preferably close to central arterial pressure, low signal to noise, determining systole and diastole, and measuring their response to a known applied pressure. The device 10 minimizes signal noise by using a relatively physically stable bed, such as the ear, as compared to a physically active bed, such as the wrist. The device 10 avoids signals that are easily contaminated by external noise and precludes a light source as a signal. The device 10 records pressure directly rather than be a modelled secondary estimate such as pulse-transit interval. The device 10 records continuously to detect transient and clinically meaningful changes, and it should have high fidelity to permit secondary estimates of stroke volume and systemic vascular resistance. Finally, the device 10 is proximate to the aortic root as possible, to provide proximate estimates of central arterial pressure.

The EMP sensor mounted on the ear meets these criteria. It is a clean signal with no external contamination and provides clean signals while a user is moving, (e.g., squatting and walking). The EMP has a clearly identifiable dicrotic notch high on the waveform much like the central waveform, and measures BP directly rather than as a secondary modelled estimate. The EMP records a continuous BP waveform. Systole and diastole are easily detected as temporally localized maxima and minima. Systolic BP is estimated by occlusion of the signal in response to increasing plunger force. It is detected by first subtracting the linearly increasing background signal, then determining the minima of the first derivative of the residual signal. The maxima of the first derivative of the residual signal defines maximal pulsatility, or diastole. These preprocessing calculations are performed by processing circuitry in the device 10.

Heart Rate Monitoring

Heart rate may be estimated from the interbeat intervals of the time of the peak BP for each pulse. This is detected as the timing of the local maxima of the waveform signal associated with the local minima of the first differential of the signal. Due to the high fidelity of the signal, the device 10 detects interbeat intervals well within 20 ms of the corresponding ECG signal. Alternatively, the multi-sensor 34 may provide for heart rate estimates by ECG recordings. ECG recordings preferably need a vector bipole distance of a least 5-10 mm for tolerable noise. Meeting an error estimate of 10% from a BP signal means on average a 50-100 ms error tolerance. The BP heart rate derivation greatly exceeds this tolerance—yielding heart rate estimates with a 20 ms precision.

Temperature Monitoring

The multi-sensor 34 may comprise a temperature sensor as a thermistor having an accuracy of, e.g., ±0.1° C. The thermistor may be embedded in a part of the casing adjacent to the scalp to provide a temperature estimate closer than a pinna temperature to core temperature. In some implementations, the radio transmitter may measure temperature. In other implementations, a no-touch thermopile may measure temperature.

Oxygen Saturation Monitoring

The multi-sensor 34 may include an oxygen saturation sensor that measures arterial oxygen saturation with a dual wavelength transmitter and a photodiode receiver for either transmitted or reflected light. To avoid the effects of compression on blood flow and saturation the device 10 may include a reflectance photodiode receiver in its shell aimed towards the back of the pinna. This provides a stable recording. Optimal positioning may be be determined by empiric adjustment. Suitable microminiature, inexpensive oxygen saturation sensors are available as COTS components.

Motion Sensing

As will be appreciated, wearability involves compromises among size, comfort, appearance, weight, component complexity, stability in adhering to the skin, and lack of interference with sleep. To address these issues in a cost-effective manner, the multi-sensor 34 may include COTS-available microminiature motion sensors. These are calibrated against human activity to provide accurate biometric information. An accelerometer may be provided as a triaxial accelerometer based on either piezoresistive or capacitance-coupled MEMS technologies. The output is sent to the radio transmitter/micro-controller for processing. The accelerometer may be affixed to the inner shell surface, and will transform the signal into outputs displaying vertical motion such as standing up or falling, general physical activity without directionality (e.g., such as washing dishes), and horizontal motion such as walking or running. In some implementations, the signal can be sent via Bluetooth to base station and then computer for final processing.

Use Cases

The device 10 may be used to detect and measure unique spontaneous physiological context phenomena (e.g. fainting), and subtle changes in dynamic variables from programmed scripted physiological states. All voluntary and involuntary processes within the body are highly coupled to each other. For example, consider the dynamic variable of blood pressure. When a subject breathes, negative and positive mechanical intra-thoracic pneumatic pressures are created that directly and mechanically affect BP. These mechanical effects are immediately detected by arterial baroreceptor cells, which send neural baroreflex messages to the arteries and veins to either dilate or contract causing BP changes. Neural stretch receptors in the lungs initiate neurologically mediated reflexes that control heart rate and BP, and so on.

Every process is coupled to many other processes and they all have their own cyclicity or impulse response function. Such coupling mechanisms include, but are not limited to: neurological, biochemical (e.g., sugar and O2, CO2), hormonal, mechanical, electrical field and current, magnetic field, and psychological will. Moreover, these processes may utilize the same neural pathways, as is the case with the vagus nerve control of heart rate. There often exists a hierarchy of processes within the autonomic control center of the brain, analogous to the hierarchy of interrupts in a microprocessor, and this hierarchy can nonlinearly affect the expression of many dynamic physiological variables.

Thus, considering the dynamic nature of living organisms, the device 10 can operate so as to make "active" measurements only when the firmware recognizes a reproducible precise user-defined physiological context; this will reduce confounding effects on the measurement and make for a more meaningful measurement. For example, very subtle changes may be determined from extracted features in the dynamic variables acquired by the device 10. The is beneficial to downstream analysis because machine learning (ML) and artificial intelligence (AI) is largely based on "neural networks" adjusting their weighting of the various features extracted from continuous signals, etc. Thus, any effort to reduce confounding influences help the ML and AI health industries moving forward.

The device 10 may be used by subjects who follow simple timed protocols involving use of daily activities to manufacture the physiological context. For example, if a subject performs the same protocol every day, or every hour, the device 10 may test for subtle effects of a drug or therapy. Repeating the physiological context will determine how the drug or therapy is affecting non-confounded measurements within the protocol. In another example, if a subject performs a scripted protocol while sick, early indications of future serious problems may be detected by providing data to AI and ML systems for analysis. Physicians may then therapeutically intercept and prevent further weakening of the system before an irreversible failure mode occurs while the subject is not otherwise micro-stressed by a cold or flu virus.

In addition to the above, because the device provides 10 for precise control of the motor in real-time, pre-programmed straining protocols may be applied (i.e., varying strain as a function of time). By controlling the rate and direction of strain the device can create protocols such as strain oscillations at any number of frequencies, or random strain, across the vascular ear bed; this enables the device 10 to be an "active" sensor. By "active," it is meant that the device 10 is actively stimulating the tissue mechanically and measuring the tissue response using the force/magnetic sensor. Thus, the device 10 can interrogate elastic properties of the arteries. For instance, applying varying frequencies of strain oscillations would show how the tissue responds at each frequency. Thus, a spectrum of the "elasticity" of the arterial beds within the ear vise may be produced. The measured "elasticity" may be tested as a function of disease state or pharmacological intervention to provide a completely new type of micro-measurement of vascular behavior.

With the motor control, if a subject is known to have spontaneous fainting episodes, the device 10 may capture one because of its continuous mode of operation. If the subject does faint, the device 10 will detect a drop in BP pressure and the motorized clip will stimulate the vascular bed to see if there is a measurable difference in the micro-programmed stimulated response during fainting, as compared to when the subject is not fainting. To make this the best measurement possible, free from confounding factors, these micro-programmed stimulated responses are performed in otherwise similar physiological contexts. In this case, this context can be defined: 1) during the BP minimum phase of the arterial baroreflex (when arterial compliance is known to be minimum), 2) near the end of diastole when the arterial BP is low, and 3) at the end of respiration again when the arterial BP is low. Thus, if the micro-programmed stimulated responses are measured in this exact same physiological context during the faint, and is compared with many micro-programmed stimulated responses in the exact same physiological context not during the faint, it can be determined if some dynamic elastic properties are indeed different during fainting. In other words, in real-time, the device 10 can eliminate all potential confounding factors by performing micro programmed stimulated responses in the same precise physiological context both during fainting and during non-fainting (fainting being the only independent variable). The device 10 can be programmed to perform real-time micro programmed stimulated responses in the exact defined physiological context; this reduces confounding factors, thereby yielding more unconfounded measurements. All this can be set up in the firmware of the device. Thus, the micro-programmed stimulated responses are a unique method for acquiring minimally-confounded measurement in real-time.

Testing and Validation

A component of continuous BP devices is the ability to periodically compress an arterial bed to occlusion with a known pressure such that continuously acquired BP waveforms can be transformed to BP estimates. The device 10 detects waveforms as micron-level fluctuations in ear pinna thickness. The multi-sensor 34 detects these fluctuations by compressing the ear on command with a known range of forces, which permit estimations of pressure. To annotate systolic and diastolic BPs during compression, pulse pressure of the waveforms are delineated. Diastolic BP is derived from the lowest force that causes a drop in measured waveform pulse pressure, and systolic BP is derived from the lowest force that abolishes significant pulse pressure in the measured waveform. These provide benchmark positions on the BP waveforms to calibrate. FIG. 5 shows pulse contours with and without an occluding pressure.

Another criterion is the ability of the device 10 to respond accurately compared to the Finapres to simple, well-known physiologic maneuverers. The responses of pinna BP and Finapres BP may be compared to paced breathing, isometric leg extension, squatting and standing, and the Valsalva maneuver in twenty consenting subjects. The responses may be compared with standard linear correlation methods. Finapres fingertip BP waveforms may be used because fingertip BP methods are a practical method for beat-to-beat BP measurements in clinical research. These are key technologies in many physiology research groups. The alternative is intra-arterial catheterization, but that is invasive and not practical in many environments. FIG. 6 shows a comparison of simultaneous sequences from the Finapres sensor (top) and an early version of the magnet sensor (bottom).

The arm cuff brachial BP can be compared to device pinna BP. Arm cuff BP will be used because it is the standard BP method for most large epidemiologic and clinical trials. Arm cuff BP is usually higher than aortic BP due to superimposed reflected waveforms from the peripheral beds, and the difference is higher in younger subjects. The differences between central and radial systolic BP are in the range of 7-15 mm Hg. A transform function will be derived between pinna BP and arm cuff BP with the Alpha prototype. BP will be estimated simultaneously with these two methods in 105 adults distributed evenly by sex and by age in 7 decadal bins using office BP. The transform relationship between the two methods will be derived, including the variables age, sex, and weight. FIG. 7 shows a comparison of arm cuff and sensor pressures in 3 healthy subjects.

Tilt table testing using the Italian protocol will have beat-to-beat BP estimated simultaneously from a fingertip cuff and from the pinna BP device. Waveform signals of 100 sequential beats sampled at 200 Hz will be collected digitally, synchronized, and analyzed off-line. Two analyses may be conducted: i) systolic and diastolic BP will be correlated on a beat-to-beat basis, and ii) waveform shapes will be correlated with measurements taken every 5 ms. These data both compare pinna and fingertip BP, and their waveforms. These data will be used for testing models for estimating stroke volume from pinna BP waveforms.

There are three sources of noise: intrinsic noise within the device (so-called 1/f electronics noise), noise at the tissue-device interface, and extrinsic contaminating noise. The BP waveform from the device do not use optical inputs; this minimizes extrinsic noise due to changes in ambient lighting. In an implementation, sterilized replaceable adhesive foam strips may be used to secure the device 10 to the ear. This would ensure sterility and reduce the tissue-device noise related to subject motion, etc.

The device 10 may be tested for tissue/device interface noise, resistance to realistic temperature extremes, water immersion, and stability over time. The device 10 will be secured to the pinna by the pressure necessary to detect a signal, which may be in the range of 20-30 mm Hg. This is barely perceptible to the user. Signal/noise will be measured during graded exercise stress tests, cycling, light running, and walking up and down 2 flights of stairs. The effect of temperature extremes on the device will be assessed by storing the device at +50 C and −40 C for 30 minutes, then comparing its BP estimates with arm cuff BP. The effect of temperature extremes on the user will be tested during measurements in Alberta winter weather at −25 C and in a hot yoga studio at 42 C. Both are reasonable environments for users.

Stability to water immersion is another design consideration. Stability to sweat and water may be assessed by dampening the ear with water and separately normal saline, then comparing its BP estimates with arm cuff measurements. Signal stability over 4, 8, and 24 hours may be tested in ten subjects each with the device 10 programmed to validate BP periodically, and compare the estimated BP with the validated BP. BP will compared immediately before and after the validation step occlusion of the pinna arterial bed by the device. In the 4-hour group the device will be programmed to validate every 30 minutes, and if the signal is stable the 8 and 24-hour groups will have longer inter-validation intervals. We already have approval from the Conjoint Health Research Ethics Board in Calgary for these studies.

CONCLUSION

Thus, the present disclosure describes a device and system that may perform one or more of the following:
directly measure or indirectly determine temperature, blood pressure, peripheral capillary oxygen saturation (SpO2) and pulse rate;
wirelessly transmit results to a base station;
use commercial off-the-shelf (COTS) equipment (e.g. tablet) for the base station;
send measurements from the base station to a networked computer;
include a software development kit (SDK) to allow for third parties to develop software to access the measurements;
be able to be worn while asleep;
withstand patient exercising at an intensity equivalent to a brisk walk (~5 kph);
sense and report motion occurrence and intensity;
be water resistant;
have a sync-able real time clock;
have time stamped measurements; and/or
last 24 hours on a single charge.

While specific aspects of the disclosure have been described and illustrated, such aspects should be considered illustrative of the disclosure only and not as limiting the disclosure as construed in accordance with the accompanying claims.

What is claimed is:

1. An apparatus for monitoring biometric information of a user comprising:
a housing that includes an electropermanent magnet, a battery, a processor, and a radio transmitter;
a cap that is magnetically coupled to the housing by the electropermanent magnet when a current, controlled by the processor, is passed through a coil of the electropermanent magnet thereby compressing a portion of tissue of the user between the housing and the cap; and
a magnetic field sensor,
wherein a compressive force applied to the tissue is operably controlled by the processor which varies a magnetic field strength applied to the cap,
wherein the magnetic field sensor measures a response of the tissue while the magnetic field strength is varied to produce a signal waveform, and
wherein blood pressure is determined by the processor while varying a pulse width applied to the electropermanent magnet which in turn varies a compressive stress across tissue.

2. The apparatus of claim 1, wherein the pulse width is varied between 10-100 microseconds.

3. The apparatus of claim 1, wherein the processor determines heart rate by detecting occurrences of local maxima in the signal waveform associated with local minima of a first differential of the signal waveform.

4. The apparatus of claim 1, further comprising a multi-sensor that includes at least one of a temperature sensor, an oxygen saturation sensor and a motion sensor, wherein the multi-sensor monitors at least one of oxygen saturation, temperature, body motion from the response of the tissue.

5. The apparatus of claim 4, wherein the multi-sensor comprises a thermistor, and wherein the thermistor is embedded into the housing to detect a temperature of a user's scalp.

6. The apparatus of claim 4, wherein the multi-sensor further comprises a dual wavelength transmitter and a photodiode receiver to measure arterial oxygen saturation using either transmitted or reflected light.

7. The apparatus of claim 4, wherein the multi-sensor comprises an accelerometer that is calibrated against activity of the user.

8. The apparatus of claim 1, wherein the processor varies the current supplied to the electropermanent magnet to periodically release the portion of the tissue of the user.

9. The apparatus of claim 1, wherein varying the magnetic field strength over time and measuring the response of the tissue measures elastic properties of blood vessels within a user's body.

10. The apparatus of claim 1, wherein the processor executes instructions in accordance with a physiological context that account for interrelationships of processes in a user's body.

* * * * *